United States Patent [19]

Escribano-Crespo et al.

[11] Patent Number: 4,843,019

[45] Date of Patent: Jun. 27, 1989

[54] IMMUNOASSAY FOR DETECTING ACINO-FOETAL DIFFERENTION PROTEIN ASSOCIATED WITH CANCER OF THE PANCREAS

[75] Inventors: Maria J. Escribano-Crespo, Bagneux; Pierre Burtin, Paris, both of France

[73] Assignee: Centre National de la Recherche Scientifique, Paris, France

[21] Appl. No.: 878,838

[22] PCT Filed: Sep. 30, 1985

[86] PCT No.: PCT/FR85/00268

§ 371 Date: May 29, 1986

§ 102(e) Date: May 29, 1986

[87] PCT Pub. No.: WO86/02081

PCT Pub. Date: Apr. 10, 1986

[30] Foreign Application Priority Data

Oct. 10, 1984 [FR] France ................................ 84 15081

[51] Int. Cl.$^4$ .................... G01N 33/53; G01N 33/533; G01N 33/534

[52] U.S. Cl. .................................... 436/501; 436/506; 436/518; 436/530; 436/548; 436/526; 436/806; 436/808; 436/813; 436/804; 436/544; 436/545; 436/546; 435/7; 435/810; 530/387; 530/395; 424/85.8

[58] Field of Search ............... 436/501, 506, 518, 530, 436/548, 526, 806, 808, 813, 804, 544, 545, 546; 435/7, 810

[56] References Cited

U.S. PATENT DOCUMENTS 4,686,180 8/1987 Coggins et al. .................... 530/387

OTHER PUBLICATIONS

Escribano et al., CA vol. 105, 1986, #151087w.
Llopis et al. *Biochemica et Biophys Acta* 880, 1986, pp. 101–107.
Nilson et al., *Biochem Biophys Acta* 835, 1985, pp. 577–583.
Escribano et al. 14th *Int Cancer Congress* 1986, (Biosis Abst).
Escribano et al. *Int J Cancer* 38(2) 1982, 155–60 (Biosis Abst).
Parsa et al., *Int J. Pancreatul* 1, 1986 61–70 (Biosis Abst).
Kondo et al. CA vol. 96, 1982, #48642v.
Homma, vol. 98, 1983, #141650x.
Chemical Abstracts, vol. 96, No. 11, 15 Mar. 1982, p. 443, Ref. No. 83845k, W. H. Schmiegel et al.: "Pancreatic Oncofetal Antigen in Pancreatic Juices . . . ".
Chemical Abstracts, vol. 90, No. 21, 21 May 1979, p. 425, Ref. No. 177378n, S. R. Harvey et al. "An Immunoglobulin M (IgM) Antibody to Carcinoembryonic Antigen (CEA)–Like . . . ".
Chemical Abstracts, vol. 87, No. 23, 5 Dec. 1977, p. 451, Ref. No. 182455d, R. Fritsche et al.: "Betaonocofoetal Antigen (BOFA) Associated with Several Types . . . ".
Chemical Abstracts, vol. 87, No. 11, 12 Sep. 1977, p. 443, Ref. No. 82921n, R. Fritsche et al.: "Betaoncofetal Antigen (BOFA) Associated with Several . . . ".
Chemical Abstracts, vol. 96, No. 7, 15 Feb. 1982, p. 220, Ref. No. 48642v, Columbus, Ohio, U.S.; JP-A-81 135 422 (Sanyo Chemical Industries Ltd.) 22.10.1981.
Chemical Abstracts, vol. 91, No. 21, 19 Nov. 1979, p. 479, Ref. No. 173027W, K. Nishia et al.,: "Assay of Pancreatic Carcinoembryonic Antigen in Pancreatic . . . ".
Chemical Abstracts, vol. 85, No. 17, 25 Oct. 1976, p. 463, Ref. No. 121577g, T. Yamanoto et al.,: "Heterogeneity of Carcinoembryonic Antigen . . . ".
Chemical Abstracts, vol. 95, No. 23, 7 Dec. 1981, p. 497, Ref. No. 201826j, T. Homma et al.: "A Pancreatic Onocofetal Antigen: Its Partial . . . ".
Chemical Abstracts, vol. 98, No. 17; 25 Apr. 1983, p. 434, Ref. No. 141650x, T. Homma: "Pancreatic Oncofetal Antigen (POA) Its Characterization . . . ".

*Primary Examiner*—Howard E. Schain
*Assistant Examiner*—Garnette D. Draper
*Attorney, Agent, or Firm*—Blakely, Sokoloff, Taylor & Zafman

[57] ABSTRACT

The invention relates to acino-fetal differentiation proteins associated with cancer of the pancreas, these proteins being mannoside-containing glycoproteins of average apparent molecular mass chosen from: 120 KD, 94 KD and 58 KD.

The invention also relates to a method for preparing these proteins, an antiserum against these proteins and the method for preparation thereof, monoclonal antibodies against these proteins and the method for preparation thereof, and compositions for diagnostic or therapeutic use containing these proteins or antibodies.

3 Claims, No Drawings

IMMUNOASSAY FOR DETECTING ACINO-FOETAL DIFFERENTION PROTEIN ASSOCIATED WITH CANCER OF THE PANCREAS

The present invention relates to acino-fetal differentiation proteins associated with cancer of the pancreas, to their purification, to a specific antiserum and the preparation thereof, to monoclonal antibodies specific for these proteins and the process for preparation thereof, and also to the compositions for diagnostic use and therapeutic use containing them.

The demonstration of the presence, in extracts of fetal pancreas, of antigens similar to those of pancreatic tumor cells is known.

Human oncofetal pancreatic antigens have been identified, having a molecular weight of 40 KD (POA-1) [banwo o., Versey J. and Hobbs J. R., New Oncofetal antigen for human pancreas. Lancet, 1: 643–645, 1974 ; Hobbs J. R., Knapp, M. L. and Branfoot A. G. Pancreatic oncofetal antigen (POA): its frequency and localisation in humans. Oncod. Biol. and Medicine, 1: 37–48, 1980], 800 and 900 KD (POA-2) [Gelder F. B., Resse C. J., Moossa A. R., Hall T. and Hunter R. Purification partial characterization and clinical evaluation of a pancreatic oncofetal antigen. Cancer Res. 38: 313–324, 1978] and 1,000 KD (PCAA) (Shimano T., Loor R. M. Papsidero L. D. et al. Isolation, characterization and clinical evaluation of a pancreas cancer associated antigen. Cancer., Supplement, 47: 1602–1620, 1981]. However, none of these antigens is specific to cancer of the pancreas, since they occur in tissues other than pancreatic cancerous tumors.

The present invention relates to acion-fetal (sic) differentiation proteins associated with cancer of the pancreas, these proteins being mannoside-containing glycoproteins, of average apparent molecular mass chosen from: 120 KD, 94 KD, 75 KD and 58 KD.

The present invention also relates to a method for preparing these proteins, wherein a soluble homogenate of human fetal pancreas is prepared and wherein a fraction consisting of mannoside-containing glycoproteins is isolated.

The method for preparing these antigens comprises the following stages:
(a) a soluble homogenate of human fetal pancreas is prepared,
(b) the homogenate is treated by affinity column chromatography using concanavalin A coupled to a gel in order to bind the said proteins,
(c) the proteins in question are eluted, and
(d) the proteins obtained are optionally purified.

The preparation of the homogenate is described in Example 1.

Young fetuses of gestational age less than 6 months, and preferably less than 5 months, are used because the proteins according to the invention do not appear in the adult pancreas and because rabbits injected with pancreas from fetuses older than 6 months did not produce detectable antibodies.

In a particular embodiment, a gel of Sepharose 4B coupled to concanavalin A, marketed by Pharmacia, was used. The unbound fraction is removed, and the bound fraction is eluted using a specific ligand, e.g. 0.2 M α-methylmannoside. The eluted bound fraction is then dialyzed by a conventional technique and the proteins are separated, for example by preparative electrophoresis. The peaks corresponding to the proteins according to the invention have been identified beforehand by qualitative electrophoresis.

The acrylamide gel fractions charged with proteins according to the invention are then removed and the proteins are extracted therefrom by electroelution in a dialysis tube against PBS phosphate buffer (saline solution 0.15 M NaCl buffered to pH 7 with potassium phosphate buffer, 0.01 M final concentration). The proteins are dialyzed against distilled water and lyophilized. A characterization of the proteins according to the invention is described in Example 6.

To separate the differentiation proteins, the techniques of immune binding to the monoclonal antibodies can also be used.

The present invention also relates to an antiserum against the antigens according to the invention.

By application of the blotting technique (after acrylamide gel electrophoresis—PAGE—the proteins which have migrated into the gel are transferred electrophoretically to a nitrocellulose sheet; this sheet is then treated as in the NIF technique), this antiserum recognizes, in the extracts of fetal pancreas, 4 constituents of average apparent molecular mass 120, 94, 75 and 58 KD (to within 10%).

The present invention also relates to a method for preparing this antiserum which comprises the following stages:
(a) an animal is injected with an extract of human fetal pancreas less than 6 months of age,
(b) the animal is bled and an antiserum recovered,
(c) this antiserum is decomplemented,
(d) the decomplemented antiserum is absorbed,
(e) the absorbed decomplemented antiserum is centrifuged, and
(f) the specific antiserum is recovered.

The animal is preferably injected with an extract of fetal pancreas less than 5 months of age.

This antiserum is prepared, according to the protocol described in Example 2, against crude pancreatic extracts prepared as described in Example 1. In the particular embodiment described in Example 1, only the bleedings Nos. 4 and 5 are positive in a test for the presence of antibody.

In an embodiment of the invention, the extract was injected into a rabbit. Mice and chickens, for example, can also produce an antiserum against these extracts.

To decomplement the antiserum, it is heated on a water bath at approximately 56° C. for ½ hour, according to a conventional technique. The antiserum is then made specific for fetal pancreas by absorption with different extracts, for example extracts of normal adult pancreas, normal serum, A, O and B red cells and possibly other organs.

To this end, 2 ml of normal serum are added per ml of antiserum and 250 mg of extracts of lyophilized normal adult pancreas per ml of antiserum.

To obtain the extract of normal adult pancreas, the procedure is as in Example 1, the pancreas originating from young donors who died accidentally.

The absorbed decomplemented antiserum is purified by a conventional centrifugation technique.

The purified absorbed antiserum was tested for its ability to detect the antigens by two techniques:

(A) Immune Binding to Nitrocellulose Membranes (NIF

Technique—Nitrocellulose Immunofixation Technique)

This technique is described in Example 3. It enables very small amounts of one or more antigens to be detected in complex mixtures, for example crude organ extracts or pathological sera. This technique enables as little as approximately 0.1 µg of differentiation proteins per ml to be detected in crude organ extracts or biological fluids.

The sensitivity varies with the antigen-antibody system and can range up to 0.01 µg of antigens per ml, equivalent to 0.0005% when, as for the tests collated in Table 1, the extracts are analyzed at from 20 mg/ml.

By this technique, the antiserum proved positive for the extracts of fetal pancreas, the tumors of pancreas and hepatic metastases of a primary cancer of the pancreas. In contrast, other extracts of adult or fetal organs detailed in Table I proved negative.

TABLE I

EXTRACTS OF NORMAL ORGANS AND NORMAL SERUM

| Organ$^\beta$ | Fetal$^\beta$ | Adult$^\beta$ |
|---|---|---|
| Pancreas | + | — |
| Liver | — | — |
| Stomach | — | — |
| Lung | — | — |
| Intestine | — | — |
| Kidney | — | — |
| Spleen | — | — |
| Normal serum | — | — |

The extracts are pools of organs used at a decreasing concentration from 20 mg/ml. NT=Not Tested By this same technique, 100% of the sera of patients suffering from cancers of the pancreas were positive (N=17), whereas the serum of patients having other tumors was negative (see Table II).

TABLE II

PATHOLOGICAL SERA

| Pathological sera$^\beta$ | Number tested$^\beta$ | Number positive$^\beta$ |
|---|---|---|
| Cancer pancreas | 17 | 17 |
| Cancer stomach | 2 | 0 |
| Cancer colon | 2 | 0 |
| Cancer lung | 2 | 0 |
| Cancer kidney | 2 | 0 |

The sera are used at Lg2 dilutions from the normal concentration.

(B) Immunohistology on Sections Fixed in Ethanol or Bouin's Fluid

The method used is described in Example 4. Using either the immunofluorescence technique or the indirect immunoperoxidase technique, the antiserum labels fetal acinar cells up to about the 6th month of pregnancy, and is negative for other fetal or adult organs. It labelled all the cancers of the pancreas analyzed and was negative for a large variety of other types of cancer. The results of the immunohistology are detailed in Table III.

TABLE III

Reaction of the anti-(fetal pancreas) antiserum in NIF and immunohistology

| Cancer | Number tested | Positive | Negative |
|---|---|---|---|
| Pancreas | 18 | 18 | 0 |
| Liver | 11 | 0 | 11 |
| Stomach | 8 | 0 | 8 |
| Colon | 10 | 0 | 10 |
| Salivary glands | 4 | 0 | 4 |
| Lung | 4 | 0 | 4 |

TABLE III-continued

Reaction of the anti-(fetal pancreas) antiserum in NIF and immunohistology

| Cancer | Number tested | Positive | Negative |
|---|---|---|---|
| Bladder | 6 | 0 | 6 |
| Gall bladder | 6 | 0 | 6 |
| Breast | 3 | 0 | 3 |
| Prostate | 7 | 0 | 7 |
| Normal tissues | 20 | 18 | 2 (±) |
| Fetal pancreas 6 months and less | | | |
| Fetal pancreas more than 6 months | 16 | 8 | 8 |
| Adult pancreas | 6 | 0 | 6 |
| Duodenum | 4 | 0 | 4 |
| Stomach | 2 | 0 | 2 |
| Gall bladder (ducts) | 5 | 0 | 0 |
| Salivary glands | 3 | 0 | 3 |
| Chronic pancreatitis | 11 | 2 | 9 |

The instances of chronic pancreatitis constitute a special case, since they are generally negative but, in some cases, a labelling is observed which is similar to that found in the zones around a tumor.

The antiserum according to the invention hence enables serum and tissue levels to be detected which are too small to be assayed by precipitation, the threshold of sensitivity of which is about 10 µg/ml.

The Applicant Company has demonstrated that the proteins according to the invention appear not only in pancreatic tumors but also in pretumoral lesions. These differentiation proteins are hence of value, in addition, as pretumoral markers.

In effect, during experimental chemical carcinogenesis in hamsters, they are expressed at about the second month, whereas the first tumors are only detected histologically at about the 8th month.

In man, these antigens express themselves intensely not only in the cancers but also in the pretumoral markers.

The table which follows shows other analytical results which demonstrate the specificity of these differentiation proteins for other fetal and adult normal tissues, using the techniques of NIF and immunohistology.

TABLE IV

| Tissue | Fetal | | Adult | |
| | NIF | Hist | NIF | Hist |
|---|---|---|---|---|
| Pancreas | + | + | — | — |
| Liver | — | — | — | — |
| Lung | — | — | — | — |
| Stomach | — | — | — | — |
| Colon | — | — | — | — |
| Small intestine | — | — | — | — |
| Salivary glands | NT | NT | NT | — |
| Bladder | " | — | — | — |
| Gall bladder | " | — | " | — |
| Muscle | — | — | " | — |
| Skin | — | NT | — | NT |
| Brain | — | " | — | " |
| Spleen | — | — | — | — |
| Kidney | — | — | — | — |
| Serum | — | — | — | — |

+positive reaction;
—negative reaction;
NT not tested

These differentiation proteins according to the invention can also be applied in the production of specific antibodies.

Thus, the Applicant Company has carried out the preparation of monoclonal antibodies specific for the differentiation proteins according to the invention.

For this reason, the present invention relates to monoclonal antibodies specific for the differentiation proteins of apparent molecular mass 120 KD, 94 KD, 75 KD and 58 KD.

The present invention also relates to a method for preparing these monoclonal antibodies, which comprises the following stages:

(a) a mouse is immunized with at least one of the differentiation proteins,
(b) cell fusion of spleen cells from these mice is carried out with an $SP_2$ myeloma,
(c) the hybridomas obtained are cultured in a suitable medium,
(d) the cultures are selected by screening,
(e) the hybridomas which are positive on screening specifically with fetal pancreas are retained and cloned, and
(f) the monoclonal antibody is isolated and optionally purified.

To prepare these antibodies, the classical hybridization technique, as developed by Kohler and Milstein in 1975, is hence used, immunizing mice, for example BALB/C mice, with the fraction, prepared beforehand, of a homogenate of fetal pancreas less than 6 months of age, purified on concanaval in A. In a particular embodiment of the invention, differentiation proteins prepared according to the invention from fetal pancreata 3 to 4 months of age were used to immunize the mice.

For the screening, that is to say the selection of the productive hybridomas, use is made, for example, of the NIF technique already described. The cultures are tested with various extracts, for example extracts of normal adult pancreas, normal adult serum and fetal serum, and an extract of fetal pancreas, and only the cultures which react specifically with the fetal pancreas are retained.

The monoclonal antibodies are then selected by classical techniques. Thus, it is possible to use the "Immuno Blot" technique, employing SDS-PAGE (Example 5), a technique also known by the name "Western Blot" and described by Towbin et al. (Electrophoretic Transfer of proteins from polyacrylamides gels to nitrocellular sheets procedure and some application, Prot. Nat. Acad. Sci. USA 76, 1979 page 350-354).

The monoclonal antibodies are then isolated in the supernatant of the selected hybridoma cultures, by one of the usual techniques.

Monoclonal antibodies can also be obtained from ascites, by injecting mice with the cell which produces the monoclonal antibody.

In this manner, the Applicant Company has isolated two monoclonal antibodies which are specific for the differentiation protein according to the invention of average molecular mass 120 KD.

It is demonstrated by typing that the antibody is of the IgG type.

The antibodies can then be isolated by affinity chromatography on protein A bound to sepharose, for example, eluting at a pH of between 3 and 6.

The present invention hence also relates to compositions for diagnostic use containing, by way of active component, at least one differentiation protein or a monoclonal antibody according to the invention and an acceptable substrate, for example in the form of kits for immunodiagnosis according to a mechanism based on antibody-antigen reactions.

The differentiation proteins and the monoclonal antibodies according to the invention are also useful as specific tumoral and pretumoral markers which can be used for imaging.

Thus, the present invention relates to the compositions for diagnostic use containing the differentiation proteins or the monoclonal antibodies according to the invention, labelled.

For this use, the labelling can be produced by any label, especially fluorescent, radioactive or paramagnetic labels.

Finally, the present invention also relates to the compositions for therapeutic use containing at least one differentiation protein or a monoclonal antibody according to the invention, conjugated to an active principle.

EXAMPLE 1

Preparation of Extracts of Fetal Pancreas

The pancreas is removed from fetuses in good condition after therapeutic abortion at 3 to 4 months of pregnancy, and rapidly immersed in an antiprotease solution containing aminocaproic acid (0.4%) and aprotinin (40 Kallikrein units/ml), for example the aprotinin Trasylol ® marketed by Sigma.

The pancreas, in the proportion of 100 mg/ml of antiprotease solution, is ground as soon as possible after removal with an Ultraturax grinder for a few minutes in the cold.

The extract is centrifuged at 20,000 rpm for ½ hour, and the supernatant is divided into aliquots and stored at −80° C.

These extracts contain between 5 and 8 mg of proteins per ml.

EXAMPLE 2

Preparation of the Antiserum

The pancreas extract described above is injected into a rabbit according to the following protocol:

Day 1: 1 ml of extract+1 ml of Freund's complete adjuvant in intradermal injections at several points of the back.
Day 24: Same procedure as Day 1.
Day 44: Trial bleeding No. 1.
Day 54: Re-immunization as Days 1 and 24.
Day 78: Trial bleeding No. 2.
Day 98: Further injection as above.
Day 110: Trial bleeding No. 3.
Day 150: Intravenous injection without adjuvant (centrifuged completely clear solution).
Day 156: Trial bleeding No. 4.
Day 186: Further intravenous injection.
Day 192: Bleeding No. 5.

The serum is then decomplemented by bringing it to a water bath at 56° C. for approximately 30 minutes, and then absorbed with extracts of normal adult pancreas, normal serum and A, O and B red cells.

EXAMPLE 3

NIF Technique

Cut out a piece of nitrocellulose of suitable size (nitrocellulose membranes BA85, Schleicher and Schull - Dassel, GDR).

Deposit the solution in which the antigen is sought in 1- to 5-μl microdroplets. The concentration is chosen in accordance with the sensitivity desired. The dilutions of the antisera are carried out in a 2% strength solution of egg white ovalbumin, in distilled water, marketed by Sigma.

Allow to dry. Rinse with PBS.

Incubate for 1 hour at 4° C. in a saturating protein solution (2% strength egg white ovalbumin solution, in distilled water, marketed by Sigma) to block the binding sites on the membrane not occupied by the antigen.

Rinse with PBS. Incubate with the antiserum. In this case, for the absorbed anti-(fetal pancreas) serum, it is used diluted 1/1,000 overnight at 4° C.

Wash the filter copiously to remove the antiserum completely.

Incubate with antibody to rabbit IgG conjugated to peroxidase (Institut Pasteur Production), diluted 1/2,000, for 2 hours at 4° C.

Wash again copiously with PBS.

Visualize the enzyme reaction by incubation in the peroxidase substrate: 0.01% $H_2O_2$ and the chromogen. The latter can be either chloronaphthol (Sigma), giving a blue coloration, or 3,3'-diaminobenzidine (DAB, Merck), giving a brown coloration. The former is dissolved to a concentration of 3 mg/ml in methanol and then diluted 5-fold in PBS. The second (DAB) is dissolved directly in PBS (0.5 mg/ml). In both cases, add hydrogen peroxide to a final concentration of 0.01%, as stated above.

When the reaction is developed (stabilization of the color), wash with distilled water and, for DAB, fix the color by washing with $10^{-2}$ M HCl.

EXAMPLE 4

Immunohistology

The sections of organs, fixed either in ethanol, or in formalin, or in Bouin's fluid, are included in paraffin wax. Deparaffinize, hydrate and inhibit endogenous peroxidase.
(1) Incubate with 2% strength bovine serum albumin (BSA) in distilled water for 1 hour at 4° C.
(2) Incubate with the anti(fetal pancreas) antiserum diluted 1/25 in 1% strength BSA for 4 hours at 4° C.
(3) Wash 3 times 10 minutes in PBS.
(4) Incubate with antibodies to rabbit IgG conjugated to peroxidase (Institut Pasteur Production) diluted 1/100 in PBS.
(5) Wash 3 times 10 minutes in PBS.
(6) Visualize the enzyme reaction in a bath of 0.01% strength $H_2O_2$ and aminoethylcarbazole.

EXAMPLE 5

Immunoanalysis on Nitrocellulose Spots after SDS-Acrylamide Gel Electrophoresis

The SDS-PAGE technique is employed in 10% strength acrylamide gels in Tris-glycine buffer pH 8.3, containing 0.1% of SDS [Laenmli U.K. cleavage and structural proteins during assembly of head of the bacteriophage Nature (Lond. 227: 680–5 (1970)].

The proteins are transferred to nitrocellulose membranes in one Biorad transfer cell at 4° C. under a constant current of 100 mA for 16 hours at pH 8.3 (Towbin). The spots are visualized as in the NIF technique.

EXAMPLE 6

Characterization of the Specific Differentiation Proteins of Pancreata by the Immunoblot Technique after Acrylamide Gel Electrophoresis Homogenates of tumoral adult pancreata and fetal (17, 20, 25 and 32 weeks) pancreata are subjected to analysis by SDS-PAGE and stained with Coomassie Blue or transferred to nitrocellulose membranes.

Later, the anti-(fetal pancreas) serum has revealed several bands corresponding to the various differentiation proteins.

From the intensity of the staining, most of the proteins are almost absent in the 32-week pancreata.

The adult pancreata have not been stained.

In one tumor, two proteins are present, whereas in another the protein of molecular mass 120 K is mainly expressed.

Evaluation of the intensity of the staining relative to the reference shows that, in all cases, the differentiation proteins are present in small amounts relative to the total amount of proteins in the crude homogenates.

We claim:

1. In an immunological assay useful for the detection of pancreatic tumors, pretumoral lesions of pancreas and normality of fetal pancreas the improvement which consists of using as marker protein an acino fetal differentiation protein (AFDP) associated with cell-multiplication, said protein being a manoside containing glycoprotein of average apparent molecular mass chosen from: 120 KD, 94 KD, 75 KD and 58 KD, said detection involving the use of a composition containing a monoclonal antibody corresponding to said protein.

2. The method of claim 1, in which the differentiation protein or antibody is labelled.

3. The method of claim 2, in which the labelling is radioactive, paramagnetic or fluorescent.

* * * * *

UNITED STATES PATENT AND TRADEMARK OFFICE
CERTIFICATE OF CORRECTION

PATENT NO. : 4,843,019
DATED : 06/27/89
INVENTOR(S) : Escribano-Crespo et. al.

It is certified that error appears in the above-identified patent and that said Letters Patent is hereby corrected as shown below:

Title page:

| ITEM | DESCRIPTION |
|---|---|
| [54] | delete "IMMUNOASSAY FOR DETECTING ACINO-FOETAL DIFFERENTION PROTEIN ASSOCIATED WITH CANCER OF THE PANCREAS"<br><br>insert --IMMUNOASSAY FOR DETECTING ACINO-FOETAL DIFFERENTIATION PROTEINS ASSOCIATED WITH CANCER OF THE PANCREAS-- |
| [30] | FOREIGN APPLICATION PRIORITY DATA<br>delete "Oct. 10, 1984"<br>insert --Oct. 01, 1984-- |

Signed and Sealed this

Tenth Day of July, 1990

Attest:

HARRY F. MANBECK, JR.

*Attesting Officer*     *Commissioner of Patents and Trademarks*